United States Patent [19]

Gitlitz et al.

[11] 4,324,798
[45] Apr. 13, 1982

[54] FUNGICIDAL BIS(SUBSTITUTED PHENYL)ALKYLTIN COMPOUNDS

[75] Inventors: Melvin H. Gitlitz; David A. Russo, both of Edison, N.J.

[73] Assignee: M&T Chemicals Inc., Woodbridge, N.J.

[21] Appl. No.: 195,276

[22] Filed: Oct. 8, 1980

[51] Int. Cl.³ .................... A01N 55/04; C07F 7/22
[52] U.S. Cl. .................... 424/288; 260/429.7
[58] Field of Search .................... 424/288; 260/429.7

[56] References Cited

U.S. PATENT DOCUMENTS

| | | | |
|---|---|---|---|
| 3,031,483 | 4/1962 | Koopman et al. | 260/429.7 |
| 3,471,539 | 10/1969 | Suzuki et al. | 260/429.7 |
| 3,475,472 | 10/1969 | Suzuki et al. | 260/429.7 |
| 3,475,473 | 10/1969 | Tahara et al. | 260/429.7 |

FOREIGN PATENT DOCUMENTS 2608698 10/1976 Fed. Rep. of Germany .
40-13261 4/1965 Japan .

Primary Examiner—Dolph H. Torrence
Attorney, Agent, or Firm—Stanley A. Marcus; Donald G. Marion

[57] ABSTRACT

Asymmetrically substituted triorganotin compounds of the general formula

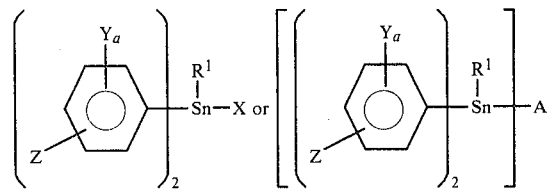

wherein
$R^1$ is hydrocarbyl or $-R^2COOR^3$ where $R^2$ is alkylene and $R^3$ is hydrocarbyl;
X is halogen, hydroxyl, $R^4COO-$ where $R^4$ is hydrocarbyl, $-OR^4$, $-SR^4$, $-SR^5COOR^4$ where $R^5$ is alkylene,

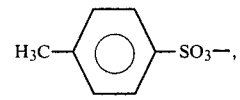

carbamate or dithiocarbamate;
Y is chlorine or bromine;
Z is halogen, alkyl, trihalomethyl, alkoxy, thioalkoxy, phenyl or methylsulfonyl;
a is 0 or 1 and
A is oxygen or sulfur are useful fungicides and exhibit little or no phytotoxicity.

13 Claims, No Drawings

FUNGICIDAL BIS(SUBSTITUTED PHENYL)ALKYLTIN COMPOUNDS

BACKGROUND OF THE INVENTION

1. Field of the Invention

This invention relates to certain novel asymmetric triorganotin compounds containing two substituted phenyl groups bonded to the tin atom and to the use of these compounds as fungicides.

2. Description of the Prior Art

Asymmetric triorganotin halides of the general formula $R^1R^2R^3SnX$ wherein each R is a hydrocarbyl group are disclosed in the prior art. German Offenlegungschrift No. 2,608,698 discloses a method for preparing this class of compounds by reacting a tetraorganotin compound of the general formula $R^1R^2SnR_2^3$ with a diorganotin dihalide of the formula $R^1R^2SnX_2$. The reaction is conducted at temperatures from 50° to 250° C. in the presence of a Lewis acid catalyst such as boron trifluoride or aluminum trichloride. In accordance with this teaching triorganotin compounds containing two phenyl and one alkyl group, such as diphenylmethyltin chloride, can be prepared by reacting diphenyltin dichloride with triphenylmethyltin, yielding equimolar amounts of triphenyltin chloride and the desired product, diphenylmethyltin chloride. Example 12 of the aforementioned publication discloses that the two products can be separated by recrystallization from hexane. The desired product is soluble and the by-product precipitates and can be removed by filtration. Depending upon the solubility product of the by-product, triphenyltin chloride, the desired compounds may still contain significant amounts of by-product. More importantly, the yield of desired compound cannot exceed 50 mole %, based on the total moles of tine present in the original reaction mixture. If substituents are present on the phenyl ring, it may not be possible to separate the two organotin halides by selective precipitation. It is well known that the presence of substituents on a phenyl ring of a triorganotin compound can alter the solubility and other physical properties of the compound. It may therefore be impossible to prepare triorganotin compounds containing two substituted phenyl groups bonded to the tin atom in the absence of the corresponding tri(substituted phenyl)tin compound using the method disclosed in German Offenlegungschrift No. 2,608,698.

Japanese Patent Publication 13261/65 discloses a number of asymmetric triorganotin compounds containing one or two substituted phenyl groups that are allegedly effective stabilizers for polypropylene. Two general preparative method are: (1) the reaction of a diorganotin dihalide with an organomagnesium halide and (2) cleavage of the corresponding tetraorganotin compounds with a halogen. The two methods are disclosed as being equivalent and there are no examples showing preparation of specific compounds. The first general method is not suitable for compounds containing two phenyl groups bonded to tin, since it will yield mixtures containing the desired product with the corresponding di- and tetraorganotin compounds. These mixtures may not be separable to obtain the desired product. The second method may yield one or more undesirable by-products, depending upon the tetraorganotin compound and the reaction conditions. Compounds of the formula

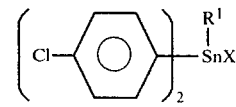

wherein (1) $R^1$ is ethyl and x is halogen and (2) $R^1$ is cyclohexyl and x is halogen or

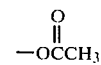

as disclosed in this publication.

It has now been discovered that bis(substituted phenyl)alkyltin compounds can be prepared in the absence of significant amounts of di- and tetraorganotin compounds and the corresponding tri(substituted phenyl)tin compounds. Some of these bis(substituted phenyl alkyltin compounds are novel, and constitute part of this invention.

DESCRIPTION OF THE INVENTION

This invention relates to certain asymmetric triorganotin compounds containing two substituted phenyl groups bonded to the tin atom and to the discovery that these compounds are effective fungicides. A further aspect of this invention relates to a method for controlling mold, mildew and other fungi on non-living substrates by the use of these asymmetric triorganotin compounds. Another aspect of this invention relates to fungicidal compositions containing these organotin compounds, either alone or in admixture with other active components, in combination with an inert carrier.

The novel asymmetric triorganotin compounds of this invention exhibit the general formula

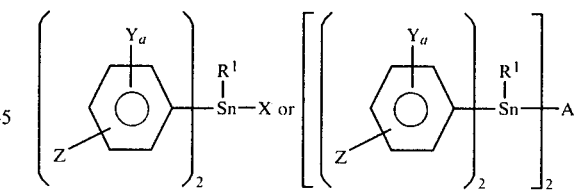

and do not contain significant amounts of organotin compounds having one or three substituted phenyl groups represented by the formula

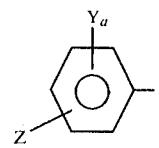

bonded to the tin atom.

In the foregoing formulae $R^1$ is selected from the groups consisting of hydrocarbyl and $—R^2COOR^3$ where $R^2$ is alkylene and $R^3$ is hydrocarbyl, A is oxygen or sulfur, X is selected from the group consisting of halogen, hydroxyl, $R^4COO—$, $—OR^4$, $—SR^4$, $—SR^5COOR^4$ wherein $R^4$ is hydrocarbyl and $R^5$ is alkylene,

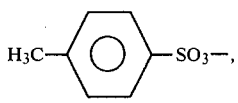

carbamate and dithiocarbamate, Y is halogen, Z is selected from the group consisting of halogen, linear alkyl, branched alkyl, aryl, trihalomethyl, alkoxy, thioalkoxy and methylsulfonyl, and a represents 0 or 1.

This invention also relates to fungicidal compositions containing one or more of the present triorganotin compounds as an active component.

In a narrower embodiment of this invention

X of the foregoing formula is halogen, hydroxyl, $R^4COO-$ where $R^4$ is lower alkyl or $p-CH_3\phi SO_3-$;

Y is halogen;

Z is halogen, lower alkoxy, lower thioalkoxy or lower branched or straight chain alkyl and $R^1$ is lower alkyl containing from 1 to 8 carbons, cycloalkyl or $-R^2COOR^3$ where $R^2$ is $-CH_2CH_2$ or $$-\overset{CH_3}{\underset{|}{C}HCH_2}-$$

and $R^3$ is lower alkyl.

In preferred embodiments of this invention

X is brome, hydroxyl, $-OOCCH_3$ or $p-CH_3\phi SO_3-$,

Z is chlorine, methoxy or methyl and a is 0 or Z is chlorine, Y is chlorine, a is 1.

This invention also provides a method for controlling the growth of fungi on non-living substrates by applying at least one of the present organotin compounds to the surface of solid substrates or incorporation the compound into liquid substrates.

The triorganotin compounds of this invention are characterized by the presence of one or two substituents on the two phenyl groups that are bonded to the tin atom. The remaining two valences on the tin atom are satisfied by (1) an hydrocarbyl group (i.e. alkyl, arul, cycloalkyl, aralkyl or alkaryl) or $-R^2COOR^3$, where $R^2$ and $R^3$ have been previously defined, and (2) a conventional anionic group such as halogen, hydroxyl, oxygen or carboxyl.

The term "aralkyl" includes the combination of an aryl and an alkyl group wherein the free valence is on the alkyl group, such as benzyl. The term "alkaryl" includes combinations of aryl and alkyl groups wherein the free valence is on the aryl group, such as tolyl.

To achieve optimum fungicidal activity the substituent represented by $R^1$ in the foregoing general formula for the triorganotin compounds of this invention is preferably a linear alkyl group containing from 1 to 8 carbon atoms or a branched chain alkyl group containing from 3 to 8 carbon atoms. Linear alkyl groups include methyl, ethyl, n-propyl, n-butyl, n-amyl, n-hexyl, n-heptyl and n-octyl. Branched chain alkyl groups include isopropyl, sec-butyl, t-butyl, iso-amyl, 2-methylpentyl, 3-methylhexyl, 2-ethylhexyl and isooctyl. Alternatively $R^1$ can also represent a cyclopentyl or a cyclohexyl group or a group of the formula $-CH_2CH_2COOC_2H_5$.

The substituent on the phenyl group bonded to the tin atom, represented by Z in the foregoing formula, can be halogen, preferably chlorine, a linear or branched alkyl group selected from the same group as the $R^1$ substituent discussed in detail hereinbefore, alkoxy or a methylsulfonyl group. When Z represents an alkoxy group it contains from 1 to 8 carbon atoms that can be in a linear or branched configuration.

When the phenyl group contains two substituents, i.e. the subscript "a" in the general formula for the compounds of this invention represents the integer 1, these substituents are conveniently halogen, most preferably chlorine due to the availability of the corresponding dichlorobromobenzene employed as the starting material for preparing the compound.

The preference for Z as chlorine, methoxy or methyl is based on availability of the corresponding substituted benzenes and the fungicidal activity exhibited by the final compounds.

The group represented by X in the foregoing general formula is halogen or any other anionic group which can replace the halogen atom on a triorganotin halide or hydroxyl group or oxygen atom of a triorganotin hydroxide or bis(triorganotin)oxide. Preferred anionic groups include hydroxide, $R^4COO-$, wherein $R^4$ represents a hydrocarbyl group containing from 1 to 12 carbon atoms, $-OR^4$, $-SR^4$,

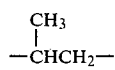

carbamate, and dithiocarbamate. Alternatively, the asymmetric triorganotin compound obtained from the cleavage reaction can be converted to the corresponding bis(triorganotin)oxide or bis(triorganotin)sulfide, in which instance A of the foregoing general formulae would represent oxygen or sulfur, respectively.

When X represents $R^2COO-$, the hydrocarbyl portion thereof can be an alkyl, cycloalkyl, aryl, alkaryl or aralkyl group. Any alkyl group or the alkyl portion of a aralkyl or alkaryl group can be linear or branched and contains from 1 to 20 carbon atoms. Typical alkyl groups include methyl, ethyl, n-propyl and iso-propyl in addition to the isometric butyl, amyl, hexyl, heptyl, octyl, decyl, dodecyl, hexadecyl and eicosyl groups. When $R^2$ is alkyl it is preferably lower alkyl and contains from 1 to 8 carbon atoms. This preference is based on the greater biological activity of lower alkyltin compounds relative to their higher alkyl homologs. When $R^2$ is aryl it can be phenyl, naphthyl, anthracenyl or phenanthryl. Representative cycloalkyl groups are cyclopentyl, cyclohexyl, cycloheptyl and cyclooctyl. Representative aralkyl groups include benzyl and $\beta$-phenylethyl. Representative alkaryl groups include tolyl and xylyl.

The present bis(substituted phenyl)hydrocarbyltin compounds are prepared by reacting a tris(substituted phenyl)hydrocarbyltin compound with chlorine, bromine, a hydrogen halide or a strong acid such as a hydrogen halide or an organosulfonic acid. During the reaction one of the substituted phenyl groups is replaced by a chlorine or bromine atom or the anionic portion of the hydrogen halide or acid. The tetraorganotin compounds employed as a starting material can be prepared using any of the known methods for synthesizing asymmetrically substituted tetraorganotin compounds. These methods are described in a test entitled "The Chemistry of Organotin Compounds" by R. C. Poller (Academic Press, New York, N.Y., 1970). A preferred method employs the reaction of an organotin trihalide $R^1SnX_3$, with an organomagnesium halide.

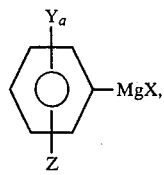

in a molar ratio of 1:3, respectively.

The preferred method for preparing the compounds of this invention employs bromine or p-toluenesulfonic acid as the cleaving agent for a tris(substituted phenyl)alkyltin compound or a tris(substituted phenyl)cycloalkyl tin compound. Bromine is gradually added to a solution of the tetraorganotin compound using a liquid halogen-containing hydrocarbon such as chloroform as the diluent. The temperature of the reaction mixture is maintained below ambient temperature, preferably from $-40°$ to $-20°$ C., to minimize the formation of undesirable by-products resulting from the replacement of more than one substituted phenyl group by bromine. When p-toluenesulfonic acid is employed as the cleaving agent the reaction can be conducted at temperatures from ambient to the boiling point of the reaction mixture.

The present triorganotin compounds effectively control a variety of undesirable fungi and other organisms which infest both living and non-living substrates. Many of the compounds are particularly effective against the organisms responsible for mildew which infest plants, particularly grape vines. Grape downy mildew is caused by the fungus *Plasmopara viticola*. Compositions containing the present compounds can be applied to grape vines and other plants and will kill or control the growth of various fungi without damaging their commercial value. The present compounds are also effective fungicides when applied to the seeds of wheat and other grains.

The organotin compounds of this invention are significantly less phytotoxic than triorganotin compounds containing unsubstituted phenyl groups. Compounds of the latter type are disclosed in U.S. Pat. No. 3,641,078. For example, a formulation containing 400 parts per million of bis(diphenylmethyltin)sulfide was sufficiently phytotoxic to kill grape seedlings. By comparison, the same concentration of bis(p-chlorophenyl)methyltin sulfide controlled grape downy mildew completely and did not damage the plants to any significant extent.

The triorganotin compounds of this invention can also be employed to prevent the growth of mildew and other fungi and a variety of non-living substrates such as paints, inks, natural and synthetic polymers, including textiles, wood, paper and other cellulosic materials.

For use as fungicides, the organotin compounds of this invention can be incorporated into compositions which comprise an inert carrier and one or more of the triorganotin compounds. The term "inert carrier" is defined as a solvent or a dry bulking agent which has substantially no fungicidal effectiveness but which provides an means whereby the present compounds can be easily diluted. These composition enable the fungicidally active ingredient to be applied in a convenient and controlled manner to plants and non-living substrates in any desired quantity. These compositions can be in the form of solids, such as dusts, granules or wettable powders, or they can be liquids such as solutions, aerosols, or emulsions. The concentration of triorganotin compound in a typical fungicidal composition will generally be in the range from about 1 to 1,000 ppm. (parts per million), more often from about 10 to 500 ppm. Compositions employed as agricultural fungicides generally contain from about 0.01 to about 3.0 pounds, preferably from about 0.1 to about 1.0 pound per acre of crop, depending on type of crop, foliage density and the severity of the infestation.

When employed as fungicides for treatment of seeds and non-living substrates, from 1.0 to 0.01 gram of triorganotin compound per kilogram of substrate usually constitutes an effective does.

For convenience in bulk handling, the compositions are generally initially formulated as concentrates which can be subsequently diluted to the desired usage level with water, organic solvent or other inert carrier just prior to use.

Dusts can be prepared by blending the triorganotin compounds with a solid inert carrier such as talc, clay, silica, pyrophylite and the like. Granular formulations can be prepared by impregnating the triorganotin compounds, usually dissolved in a suitable solvent, onto and into granulated carriers such as the attapulgites or the vermiculites, usually of a particle size range of from about 0.3 to 1.5 mm, or by coating a solid inert carrier with a wettable powder formulation of the triorganotin compounds. Wettable powders, which can be dispersed in water or oil to any desired concentration of the present compounds, can be prepared by incorporating wetting agents into concentrated dust compositions.

The triorganotin compounds of the present invention are sufficiently soluble or dispersible in the common organic solvents such as kerosene, xylene, Stoddard Solvent, acetone, and the like, that they can be used directly as solutions or dispersions in these solvents. Frequently these solutions or dispersions are dispensed under super-atmospheric pressure as aerosols. Preferred liquid fungicidal compositions for the practice of the invention herein are emulsifiable concentrates which comprise the active compound, an emulsifier, and, as an inert carrier, a solvent. Such concentrates can be extended with water and/or oil to the desired concentration of active compound for application as sprays to the plants or other substrates which are to be treated. The emulsifiers used in these concentrates are surface active agents, i.e. surfactants of the anionic, nonionic, cationic, ampholytic or zwitterionic type and normally comprise from about 0.1% to 30% by weight of the concentrate. Suitable surfactants are described in McCutcheon's Detergents and Emulsifiers—1979 Ed., Allured Pub. Co., Ridgewood, N.J., which is incorporated by reference herein. Suitable solvents for these emulsifiable concentrates include hydrocarbon such as benzene, toluene, xylene, kerosene and Stoddard Solvent and halogenated hydrocarbons such as chlorobenzene, chloroform, fluorotrichloromethane and dichlorodifluoromethane. These solvents can be used singly or in combination with one another.

The following examples disclose the synthesis of preferred embodiments of the present compounds and preparative method. All parts and percentages are by weight unless otherwise specified.

EXAMPLE 1

Preparation of bis(p-chlorophenyl)butyltin bromide

A glass reactor equipped with a mechanical agitator, addition funnel and reflux condenser was charged with 935 cc (1.5 mole) of p-chlorophenylmagnesium chloride as a 1.6 N solution in tetrahydrofuran. A solution containing 126.9 g. (0.45 mole) of butyltin trichloride and 600 cc of benzene was added to the reaction in a dropwise manner over a period of one hour. The resultant solution was heated at the boiling point for one hour, allowed to cool to ambient temperature and then combined with 500 cc of a 13% by weight aqueous solution of citric acid. The organic phase of the resultant two-phase liquid mixture was isolated and the volatile materials therein removed by evaporation under reduced pressure. The yellow-green liquid residue weighed 248.79. This residue was combined with 300 cc of iso-propanol and cooled in a dry ice-acetone mixture. The white solid that formed was isolated by filtration, washed with 20 cc of cold isopropanol and dried. The dry material melted from 58° to 60° C. and was 99% pure, as determined by vapor phase chromatography. The material was found to contain 23.43% by weight of tin and 20.47% by weight of chlorine. The calculated values for the expected product, tris-(p-chlorophenyl)butyltin are 23.25% and 20.84%, respectively. A 122.7 g (0.24 mole) portion of this material was solubilized in 520 cc of chloroform and 380 cc of methanol. The resultant solution was added to a glass reactor equipped with an addition funnel, a mechanical agitator and a water-cooled reflux condenser. The contents of the flask were cooled to $-20°$ C., at which time a solution containing 38.4 g (0.24 mole) of bromine, 200 cc chloroform and 100 cc methanol was gradually added to the reaction mixture over a 6.5 hour period. Following completion of the addition the cooling bath was removed and the reaction mixture was allowed to warm to ambient temperature during a 16 hour period, at which time the solvents and the by-product, 4-chlorobromobenzene, were evaporated under reduced pressure. The dark orange residue in the reactor was found to contain 24.62% by weight of tin, 13.00% by weight of chlorine and 18.60% by weight of bromine. The calculated values for the expected product, bis(p-chlorophenyl)butyltin bromide, are 24.78%, 14.80% and 16.68%, respectively.

Bis(p-chlorophenyl)butyltin bromide was converted to the corresponding bis(triorganotin)oxide by adding a solution containing 91.2 g (0.19 mole) of the bromide, 330 cc acetone and 397 cc of methanol to a solution containing 11.4 g (0.29 mole) of sodium hydroxide, 53 cc of water and 132 cc of methanol. The addition was gradual over a 30 minute period. Stirring of the resultant mixture was continued for an additional 30 minutes, during which time a precipitate formed. The precipitate was removed by filtration and discarded. The filtrate was concentrated to about ½ of the original volume by evaporation of solvent. One liter of water was then added to the residue and the oil which formed solidified upon standing. The solid was dissolved in a small amount of diethyl ether, the resultant solution was filtered and a semi-solid was recovered by evaporation of the ether under reduced pressure. The semi-solid was heated for one hour at from 55° to 60° C. to convert bis(p-chlorophenyl)butyltin hydroxide to the corresponding bis[bis(p-chlorophenyl)butyltin]oxide. The resultant oil was found to contain 28.20% by weight of tin and 16.93% by weight of chlorine. The calculated values for the expected product are 29.16% and 17.43%, respectively.

The oxide was converted to the corresponding bis-(p-chlorophenyl)butyltin acetate by the addition of a solution containing 3.7 g (0.06 mole) of glacial acetic acid in 25 cc of methylene chloride to a solution containing 25 g (0.03 mole) of the oxide and 100 cc of methylene chloride. The addition was gradual and was accomplished over a five minute period. The resultant solution was stirred for 10 minutes, at which time the water present was removed using anhydrous magnesium sulfate and the methylene chloride was removed by evaporation under reduced pressure. The resultant glassy solid was recrystallized using hexane. The recovered solid melted from 114° to 117° C. and was found to contain 25.99% by weight of tin and 14.98% by weight of chlorine. The calculated values for the expected product, bis(p-chlorophenyl)butyltin acetate, are 25.90 and 15.50, respectively.

EXAMPLE 2

Preparation of bis-(p-chlorophenyl)butyltin p-toluene sulfonate by reaction of tris-(p-chlorophenyl)butyltin with p-toluene sulfonic acid A solution containing 25.5 g (0.05 mole) of tris-(p-chlorophenyl)butyltin, prepared as described in the preceeding Example 1, 10.5 g (0.05 mole) of p-toluene sulfonic acid monohydrate and 50 cc of acetone was heated at the boiling point for 45 minutes. The mixture was then cooled to ambient temperature and the solid material present was recovered by filtration and dried. This solid product weighed 20.4 g melted from 186° to 188° C. and was found to contain 20.90% by weight of tin and 12.18% by weight of chlorine. The calculated values for the expected product, bis(p-chlorophenyl)butyltin p-toluene sulfonate, are 20.28% and 12.44%, respectively.

EXAMPLE 3

Preparation of various bis(substituted phenyl)alkyltin bromides

A number of bis(substituted phenyl)alkyltin bromides were prepared by reacting the corresponding tris-(substituted phenyl)alkyltin compound with an equimolar amount of bromine in a mixed chloroform-methanol solvent or p-toluenesulfonic acid as described in the preceeding Example 1. In some instances the bromide was converted to the corresponding oxide (or hydroxide) or acetate using procedures described in the preceeding Example 1.

The following table summarizes the compounds prepared, their melting point, tin content (actual and calculated) and yield, based on initial organotin reagent.

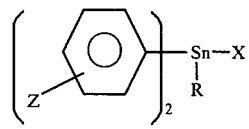

| Z | R | X | M.P. (°C.) | Yield | % Tin Found/ Calculated |
|---|---|---|---|---|---|
| o-CH$_3$O— | CH$_3$ | Br | 107–110 | N.R. | 26.83/27.74 |
| o-Cl | n-C$_4$H$_9$ | o-Clφ | 110–113 | 79% | 22.31/23.30 |
| o-Cl | n-C$_4$H$_9$ | Br | N.R.[1] | 90% | 24.66/24.79 |
| m-Cl | CH$_3$ | m-Clφ | 53–55 | >90% (crude) | 25.44/25.34 |
| m-Cl | CH$_3$ | Br | N.R.[1] | 90% | 26.77/27.18 |
| m-Cl | CH$_3$ | —OH | 96–100 | 86% | 30.52/31.75 |
| m-Cl | CH$_3$ | —OOCCH$_3$ | 115–7 | 61% | 27.75/28.54 |
| m-CH$_3$ | CH$_3$ | m-CH$_3$φ— | N.R.[1] | N.R. | 28.74/29.16 |
| m-CH$_3$ | CH$_3$ | Br | N.R.[1] | 99% | 29.72/30.77 |
| m-CH$_3$ | CH$_3$ | —OH | 104–7 | >90% (crude) | 35.31/35.65 |
| m-CH$_3$ | CH$_3$ | —OOCCH$_3$ | 117–9 | >90% (crude) | 31.33/31.66 |
| m-Cl | n-C$_4$H$_9$ | m-Clφ | N.R. | 89% | 22.78/23.25 |
| m-Cl | n-C$_4$H$_9$ | Br | N.R. | N.R. | N.R. |
| m-Cl | n-C$_4$H$_9$ | —OH | 72–5 | 73% | 27.82/28.53 |
| m-CH$_3$ | n-C$_4$H$_9$ | —OOCCH$_3$ | 97–9 | 66% | 28.26/28.50 |
| m-Cl | —⟨S⟩ | —OOCCH$_3$ | 82–4 | 94% | 23.72/23.70 |
| p-Cl | CH$_3$ | p-Clφ | 82–4 | 90% | 25.64/25.34 |
| p-Cl | CH$_3$ | Br | N.R.[1] | 98% | 27.35/27.18 |
| p-Cl | CH$_3$ | Cl | N.R. | 17% | 30.58/30.29 |
| p-Cl | CH$_3$ | —OH | 118–23 | 93% | 32.24/31.75 |
| p-Cl | CH$_3$ | —OOCCH$_3$ | 161–3 | 94% | 28.11/28.55 |
| p-Cl | CH$_3$ | p-CH$_3$φSO$_3$—[2] | 212–4 | 92% | 22.06/22.48 |
| 3,4-diCl | CH$_3$ | 3,4-diClφ | 100–4 | 72% | 19.27/20.76 |
| 3,4-diCl | CH$_3$ | —OH | >360 | 70% | 27.06/26.80 |
| 3,4-diCl | CH$_3$ | Br | 117–8 | 60% | 23.49/23.47 |
| 3,4-diCl | CH$_3$ | —OOCCH$_3$ | 189–91 | 77% | 23.11/23.70 |
| p-CH$_3$O | CH$_3$ | p-CH$_3$Oφ— | 92–5 | N.R. | 25.76/26.08 |
| p-CH$_3$O | CH$_3$ | Br | 70–5 | N.R. | 28.35/27.74 |
| p-CH$_3$O | CH$_3$ | —OH | 129–33 | 63% | 32.91/32.52 |
| p-CH$_3$O | CH$_3$ | —OOCCH$_3$ | 137/41 | 98% | 29.42/29.16 |
| p-Cl | n-C$_4$H$_9$ | p-Clφ— | 58–60 | 63% | 23.43/23.25 |
| p-Cl | n-C$_4$H$_9$ | Br | N.R.[1] | 95% | 24.62/24.78 |
| p-Cl | n-C$_4$H$_9$ | p-CH$_3$φSO$_3$— | 186–8 | 82% | 20.90/20.82 |
| p-CH$_3$ | n-C$_4$H$_9$ | p-CH$_3$φ— | 92–210[3] | 95% | 24.61/26.42 |
| p-CH$_3$ | n-C$_4$H$_9$ | p-CH$_3$φSO$_3$—[2] | 138–44 | 49% | 22.67/22.43 |
| p-CH$_3$ | n-C$_4$H$_9$ | —OOCCH$_3$ | 91–3 | N.R. | 28.19/28.50 |
| p-Cl | -(-CH$_2$)$_2$CO$_2$Et | p-Clφ— | 72–4 | 99% | 21.23/21.40 |
| p-Cl | -(-CH$_2$)$_2$CO$_2$Et | Br | N.R. | N.R. | 22.48/22.70 |
| p-Cl | —⟨S⟩ | p-Clφ— | 115–7 | 82% | 22.01/22.13 |
| p-Cl | —⟨S⟩ | Br | N.R. | N.R. | N.R. |
| p-Cl | —⟨S⟩ | —OOCCH$_3$ | 115–9 | 67% | 24.73/24.53 |

NOTES:
N.R. = not reported
[1] = product is a liquid
[2] = product obtained via reaction of corresponding tetraorganotin compound,

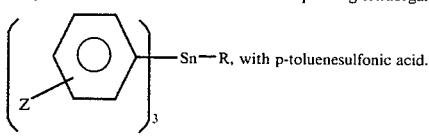

with p-toluenesulfonic acid.

[3] = boiling range under a pressure of 0.5mm of mercury.

EXAMPLE 4

Evaluation of bis(substituted phenyl)alkyltin Compounds for Control of Grape Downy Mildew Formulations containing bis(3,4-dichlorophenyl) methyltin acetate (referred to hereinafter as Compound A) and bis(p-bromophenyl)methyltin acetate (referred to hereinafter as Compound B) were prepared by dissolving each of the compounds in acetone to form a solution containing 10,000 parts per million (ppm) of the compound. A 0.9 cc portion of each solution was injected into separate 29.1 cc portions of an 80:20 weight ratio mixture of water:isopropanol, which also contained 250 ppm of a surfactant identified as Triton®X-155 (available from Rohm and Haas Company, Philadelphia, Pa.). The resultant solutions contained 300 ppm of the organotin compound and were further diluted with the aforementioned water-isopropanol-surfactant mixture to form solutions containing 75 and 19 ppm of the organotin compound. Formulations of the same concentration were prepared using two control compounds, chlorothalonil (tetrachloroisophthalonitrile) and triphenyltin hydroxide. The chlorothalonil formulations were in water. Isopropanol was employed to prepare the formulations containing triphenyltin hydroxide.

Spray solutions of each chemical at each concentration were individually and separately applied with a hand sprayer to thoroughly cover the foliage of 1-month-old grape seedlings (var. Carignana). The treated plants were kept in a greenhouse for two days after treatment, then covered and placed overnight in a bioclimatic chamber maintained at 20° C. and 100% relative himidity (R.H.). Four days after treatment, the seedlings were inoculated with freshly harvested sporangia of the downy mildew fungus, *Plasmopara viticola*, at a concentration of approximately $10^5$ sporangia/cc by spraying with a hand sprayer. The plants were then covered and held in a bioclimatic chamber at 20° C. and 100% R.H. for 3 days, after which they were returned to the greenhouse.

After 2 days in the greenhouse, the plants were inoculated a second time as previously described. Following 3 days in a bioclimatic chamber, the percent control if disease on both the foliage present at the time of treatment and that which emerged following treatment was determined. After an additional 2 days in the greenhouse and 3 days in the bioclimatic chamber, the percent control of disease was again assessed as described above. The rating system for fungus control employed a numerical scale of from 0 (no content) to 100 (100% control, no mildew present).

and diluted to concentrations of 300, 75 and 19 ppm as described in Example 3.

A repeat application test was initiated when grape seedlings (var. Carignane) were in the 4- to 6-leaf stage of growth. Spray solutions at each concentration of each chemical were applied to grape seedlings as described in Example 1 but at weekly intervals for 3 weeks. The plants were inoculated 4 days after each treatment according to the method disclosed in Example 1. Following each inoculation the plants were covered and placed overnight in a bioclimatic chamber maintained at 20° C. and 100% R.H. The final disease control evaluations were made 1 week after the final inoculation.

| PERCENT CONTROL OF GRAPE DOWNY MILDEW | | | |
|---|---|---|---|
| | Concentration, ppm | | |
| Treatment | 300 | 75 | 10 |
| Cpd A | 100% | 91% | 72% |
| Triphenyltin hydroxide | 100% TP | 100% MP | 93% SP |
| Maneb | 57% | 19% | 0% |

Notations:
TP = Plants killed from phytotoxicity
MP = Moderate phytotoxicity
SP = Slight phytotoxicity By following the foregoing evaluation procedure and employing spray solutions containing 75 ppm of four bis(substituted phenyl)alkyltin compounds that are within the scope of the present invention the following results were obtained:

| Compound | % Control of Grape Downy-Mildew |
|---|---|
| Bis(p-chlorophenyl)n-butyltin p-toluene sulfonate | 87 |
| Bis(p-chlorophenyl)cyclohexyltin acetate | 83 |
| Bis(p-chlorophenyl)n-butyltin acetate | 100 |
| Bis(p-chlorophenyl)n-butyltin bromide | 100 |

| PERCENT CONTROL OF GRAPE DOWNY MILDEW | | | | | | | |
|---|---|---|---|---|---|---|---|
| | | % Control, Foliage Present at Treatment | | | % Control Foliage Emergent after Treatment | | |
| | | Concentration, ppm | | | | | |
| Treatment | Evaluation | 300 | 75 | 19 | 300 | 75 | 19 |
| Cpd A | First | 99 | 95 | 93 | 100 | 97 | 60 |
| | Second | 98 | 90 | 75 | 99 | 75 | 25 |
| Cpd B | First | 100 | 100 | 98 | 100 VSP | 100 | 99 |
| | Second | 100 | 100 | 95 | 97 VSP | 95 | 60 |
| Chlorothalonil | First | 93 | 75 | 0 | 90 | 60 | 0 |
| | Second | 50 | 50 | 0 | 35 | 25 | 0 |
| Triphenyltin hydroxide | First | TP | 97 SP | 97 | TP | 100 SP | 60 |
| | Second | TP | 97 MP | 97 | TP | 75 SP | 25 |

Notations:
TP = Plants killed from phytotoxicity.
MP = Moderate phytotoxicity.
SP = Slight phytotoxicity.
VSP = Very slight phytotoxicity.

EXAMPLE 5

Formulations containing 10,000 ppm of compound A and triphenyltin hydroxide were prepared and diluted to 300, 75 and 19 ppm as in Example 1. A 10,000 ppm concentrate of Maneb (manganese salt of ethylenebisdithiocarbamic acid) was prepared in water from a commercially available 80% wettable powder formulation

EXAMPLE 5

Control of Various Fungi Using Representative bis(substituted phenyl)alkyltin compounds The ability of representative triorganotin compounds of this invention to control various types of fungi was evaluated with the following results. The evaluation procedure was similar to that disclosed for grape downy mildew, but using the appropriate host plant for the fungus.

Bis(p-chlorophenyl)methyltin acetate provided 100% control of both barley powdery mildew and bean powdery mildew, when applied as a foliar spray containing 400 ppm of the organotin compound.

Bis(p-chlorophenyl)methyltin hydroxide at a concentration of 400 ppm provided 90% control of rice blast.

When applied as a seed treatment a formulation containing 100 ppm of bis(p-chlorophenyl)methyltin p-toluenesulfonate provided 95% of barley powdery mildew. This compound at a concentration of 400 ppm also provided 75% control of apple scab when applied to infested plants and 97% control of apple powdery mildew in a foliar test similar to the one previously described for grape downy mildew.

Bis(p-chlorophenyl)n-butyltin bromide provided 95% control of rice blast when applied as a foliar spray at a concentration of 400 ppm, bis(p-chlorophenyl)n-butyltin p-toluenesulfonate and the corresponding acetate provided 83% and 97% control, respectively, of the same fungus at 400 ppm.

In addition to controlling fungi and other pests that can infest agricultural crops, many of the present bis(-substituted phenyl)alkyltin compounds effectively inhibit or prevent the development of mold, mildew and other fungi, on non-living substrates such as inks, adhesives, soaps, cutting oils and polymeric materials, including oil-base and water-base paints, textiles, wood, paper and other cellulosic materials. Concentrations of from about 0.01 to 10%, based on the weight of the substrate, will usually impart the desired fungicidal activity to the substrate.

What is claimed is:

1. A composition comprising a triorganotin compound of the general formula

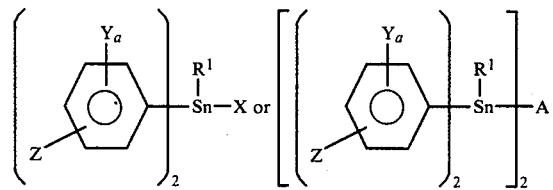

in the substantial absence of compounds of the general formulae

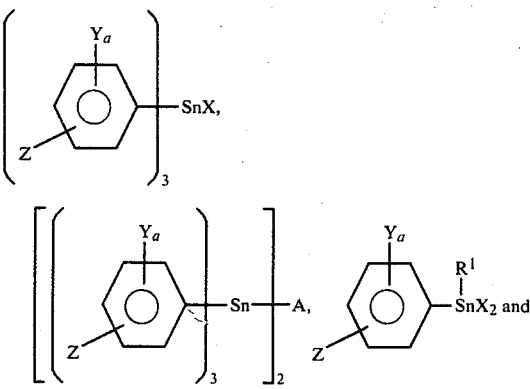

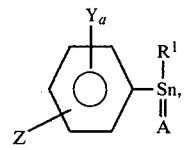

wherein $R^1$ is selected from the group consisting of hydrocarbyl and $-R^2COOR^3$ where $R^2$ is alkylene and $R^3$ is hydrocarbyl, A is oxygen or sulfur, X is selected from the group consisting of hydroxyl halogen, $R^4COO-$, $-OR^4$, $-SR^4$, $-SR^5COOR^4$ where $R^4$ is hydrocarbyl and $R^5$ is Alkylene, $H_3C$

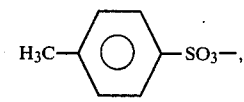

carbamate or dithiocarbamate, Y is halogen, Z is selected from the group consisting of halogen, linear alkyl, branched alkyl, aryl, trihalomethyl, alkoxy, thioalkoxy and methylsulfonyl, and a represents 0 or 1, with the proviso that $R^1$ is not ethyl when X is halogen and $R^1$ is not cyclohexyl when X is

or halogen.

2. A composition according to claim 1 wherein
   X is halogen, hydroxyl, p—$CH_3\phi SO_3$— or —$OOCR^4$ where $R^4$ is lower alkyl;
   Z is halogen, lower alkoxy, lower thioalkoxy or branched or straight chain alkyl and
   $R^1$ is lower alkyl, cycloalkyl or —$R^2COOR^3$ where $R^2$ is lower alkylene and $R^3$ is lower alkyl.

3. A composition according to claim 2 wherein any lower alkyl group contains from 1 to 8 carbon atoms and any lower alkylene group contains from 2 to 8 carbon atoms.

4. A composition according to claim 1 wherein
   Z is chlorine, methyl, methoxy or —$OOCR^4$ where $R^4$ is methyl;
   $R^1$ is methyl, butyl, cyclohexyl or —$R^2COOR^3$ where $R^2$ is —$CH_2CH_2$— or

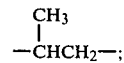

$R^3$ is ethyl and
   X is bromine, —$OOCCH_3$, —OH or p—$CH_3\phi SO_3$—.

5. A composition according to claim 4 wherein
   Y is chlorine and
   Z is chlorine.

6. A composition according to claim 1 where a is 0.

7. A composition for controlling the growth of fungi, said composition comprising an inert carrier and a triorganotin compound of the general formula

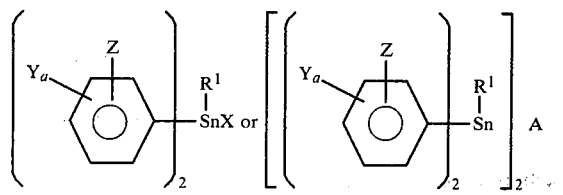

wherein $R^1$ is selected from the group consisting of hydrocarbyl and $-R^2COOR^3$ where $R^2$ is alkylene and $R^3$ is hydrocarbyl, A is oxygen or sulfur, X is selected from the group consisting of hydroxyl, halogen, $R^4COO-$, $-OR^4$, $-SR^4$, $-SR^5COOR^4$ where $R^4$ is hydrocarbyl and $R^5$ is alkylene,

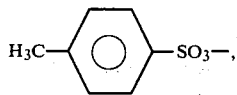

carbamate, dithiocarbamate, Y is halogen, Z is selected from the group consisting of halogen, linear alkyl, branched alkyl, aryl, trihalomethyl, alkoxy, thioalkoxy and methylsulfonyl, and a represents 0 or 1.

8. A composition according to claim 7 wherein X is halogen, hydroxyl, p—CH$_3\phi$SO$_3$— or $R^4COO-$ where $R^4$ is lower alkyl;
Z is halogen, lower alkoxy, lower thioalkoxy or lower branched or straight chain alkyl and
$R^1$ is lower alkyl, cycloalkyl or $-R^2COOR^3$ where $R^2$ is lower alkylene and $R^3$ is lower alkyl.

9. A composition according to claim 8 wherein any lower alkyl contains from 1 to 8 carbon atoms and any lower alkylene contains from 2 to 8 carbon atoms.

10. A composition according to claim 7 wherein
Z is chlorine, methyl, methoxy or $-OOCR^4$ where $R^4$ is methyl;
$R^1$ is methyl, butyl, cyclohexyl or $-R^2COOR^3$ where
$R^2$ is $-CH_2CH_2-$ or

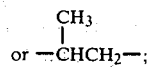

$R^3$ is ethyl and
X is bromine, $-OOCCH_3$, $-OH$ or p—CH$_3\phi$SO$_3$—.

11. A composition according to claim 7 wherein
Y is chlorine and
Z is chlorine.

12. A composition according to claim 7 wherein a is 0.

13. A composition according to claim 7 wherein said triorganotin compounds is present in a fungicidally effective amount.

* * * * *

UNITED STATES PATENT OFFICE
CERTIFICATE OF CORRECTION

Patent No. 4,324,798     Dated April 13, 1982

Inventor(s) Melvin H. Gitlitz and David A. Russo

It is certified that error appears in the above-identified patent and that said Letters Patent are hereby corrected as shown below:

Claim 1, line 15, delete "$H_3C$".

Signed and Sealed this

Twenty-first Day of February 1984

[SEAL]

Attest:

Attesting Officer

GERALD J. MOSSINGHOFF

Commissioner of Patents and Trademarks